United States Patent [19]
DeVincenzo et al.

[11] Patent Number: 5,738,514
[45] Date of Patent: Apr. 14, 1998

[54] RESILIENTLY EXPANDABLE ORTHODONTIC DEVICE

[76] Inventors: John DeVincenzo, 1312 Garden St.; Steven P. Prins, 826 Alyssum Ct., both of San Luis Obispo, Calif. 93401

[21] Appl. No.: 818,433

[22] Filed: Mar. 17, 1997

[51] Int. Cl.⁶ .................................................. A61C 3/00
[52] U.S. Cl. ............................................. 433/19; 433/18
[58] Field of Search ............................ 433/18, 19, 22, 433/24

[56] References Cited

U.S. PATENT DOCUMENTS

| | | | |
|---|---|---|---|
| 3,158,934 | 12/1964 | Waldman | 433/19 X |
| 3,798,773 | 3/1974 | Northcutt | 433/19 |
| 5,022,855 | 6/1991 | Jeckel | 433/18 |
| 5,120,218 | 6/1992 | Hanson | 433/19 |
| 5,562,445 | 10/1996 | DeVincenzo et al. | 433/19 |

FOREIGN PATENT DOCUMENTS 374163  7/1921  Germany .................................. 433/19

*Primary Examiner*—Nicholas D. Lucchesi
*Attorney, Agent, or Firm*—James B. Middleton

[57] ABSTRACT

An orthodontic appliance has two telescoping cylinders having springs therein to urge the cylinders apart. The outer cylinder is then slidably inserted into a third cylinder. The outer ends of the cylinders are attached to a patient's teeth so the springs exert a force on the teeth when the spring-urged cylinders contact the end of the third cylinder. The cylinders may be separable so the springs can be exchanged, or may be permanently fixed together. The attachments allow universal motion so the lower jaw can move to the full extent of the normal jaw without binding or destroying the appliance.

10 Claims, 2 Drawing Sheets

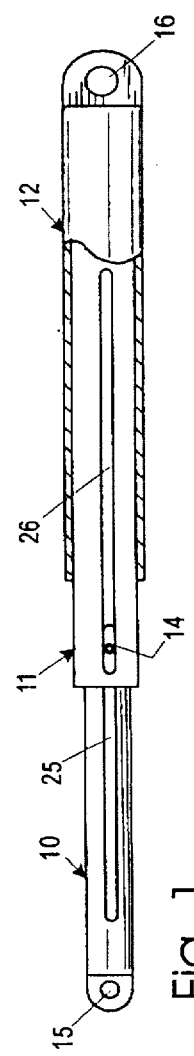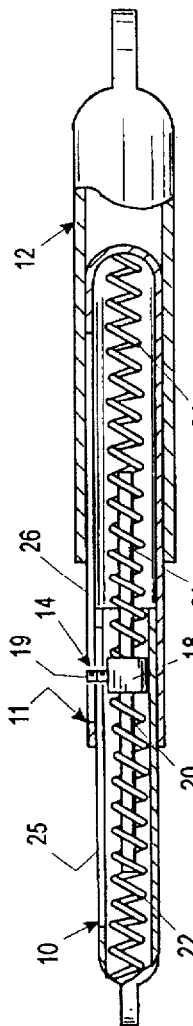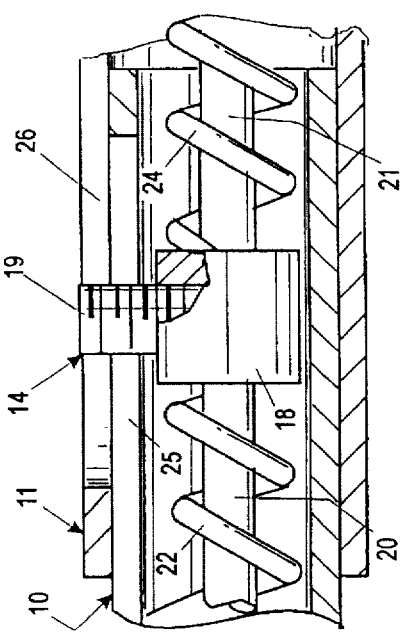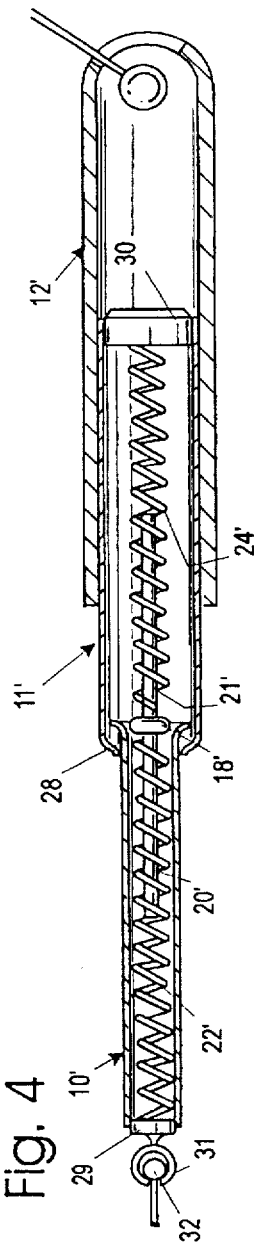

5,738,514

RESILIENTLY EXPANDABLE ORTHODONTIC DEVICE

BACKGROUND OF THE INVENTION

1. Field of the Invention

This invention relates generally to orthodontic appliances, and is more particularly concerned with a resiliently expandable arrangement that normally applies a force between the upper and lower teeth but is sufficiently extendible to allow complete normal movement of the mandible.

2. Discussion of the Prior Art

It is common in orthodontics to utilize appliances that exert a force between the maxillary and the mandibular dentitions in order to induce orthopedic and/or orthodontic correction. Early forms of such appliances comprise simply coil springs connected between the maxilla and the mandible. While these springs will exert the force needed, they are uncomfortable for the patients in that the cheek gets pinched in the coils of the spring, and food and the like accumulates in the springs. Additionally, they have been of very short life because of rapid and frequent breakage while severely restricting the movement of the mandible.

One solution to the above mentioned problems is to cover the springs as shown in the patent to Armstrong, U.S. Pat. No. 3,618,214. While such a covering diminishes the problems, it does not affect the problem of limited mandibular motion. More recent efforts at solving the problems are shown in U.S. Pat. No. 4,708,646 to Jasper and No. 4,795,342, to Jones. The Jones device has a spring enclosed within a cylinder, but still allows very limited motion. The Jasper device has a spring encased in an elastic material, and provides somewhat loose connections to give some freedom, but still does not allow full normal motion of the mandible. U.S. Pat. No. 5,562,445 discloses a very successful orthodontic device that allows full normal motion of the mandible without damage to the device. It has been found, however, that the patient's cheek will sometimes lift the device and place it in the occlusion. The patient may bite on the device, which may be painful, as well as damage the appliance.

SUMMARY OF THE INVENTION

The present invention provides an orthodontic appliance having spring means enclosed within a double cylindrical housing. In its relaxed state the device is fully extended, so the device is compressed for installation to yield the desired force. Each end of the device is arranged for swivel mounting to the teeth to allow full normal movement of the mandible in all directions. The double cylinder housing the spring means may be slidably received within another cylindrical housing to expand the range of extension of the device. Thus, the mandible can be opened to the maximum extent anatomically possible, and the device of the present invention will allow such movement, and will not be separated or damaged by such movement. Additionally, unlimited lateral excursions are obtainable with the present device. In one embodiment of the invention, the particular spring can be replaced so the orthodontist can select the spring tension desired for the particular patient. Some novel attachment means provide simplicity and sureness in the installation.

BRIEF DESCRIPTION OF THE DRAWINGS

These and other features and advantages of the present invention will become apparent from consideration of the following specification when taken in conjunction with the accompanying drawings in which:

FIG. 1 is a top plan view of an orthodontic appliance made in accordance with the present invention;

FIG. 2 is a front elevational view, mostly in cross-section, of the device shown in FIG. 1;

FIG. 3 is an enlarged fragmentary view showing the stop of the device in FIG. 2;

FIG. 4 is a view similar to FIG. 2 showing a modified form of the device;

DETAILED DESCRIPTION OF THE EMBODIMENTS

Figure 5:
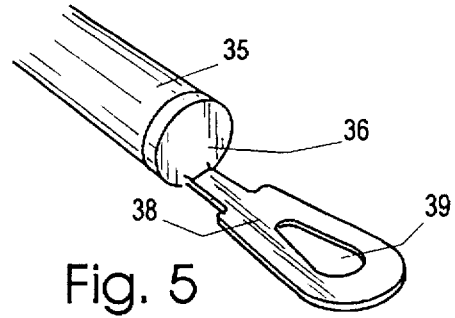
FIG. 5 is a perspective view showing an attachment means for use with an appliance of the present invention.

Referring now more particularly to the drawings, and to those embodiments of the invention here presented by way of illustration, FIG. 1 comprises a pair of cooperating telescoping cylinders 10 and 11. The cylinders 10 and 11 are then receivable into a third cylinder 12. It will be understood that the cylinders 10 and 11 house a spring, or springs, urging the cylinders apart, and there is a stop 14 to limit the relative movement of the two cylinders, primarily to prevent separation of the two cylinders.

In this embodiment of the invention, each end of the appliance defines a hole, such as the holes 15 and 16, to allow any convenient attachment means for the appliance.

With attention to both FIG. 1 and FIG. 2 it will be seen that the stop means 14 includes a body 18 having a projection 19 therefrom. Guide pins 20 and 21 extend axially in opposite directions from the body 18, the guide pins 20 and 21 serving to hold the springs 22 and 24 in proper alignment along the centerlines of the cylinders.

Each of the cylinders 10 and 11 defines a slot therein, as indicated at 25 and 26, and the projection 19 of the stop 14 extends into both slots 25 and 26. As a result, when ends of both slots 25 and 26 engage the stop 14, the cylinders 10 and 11 cannot further separate.

FIG. 3 shows the stop 14 enlarged, and it will be noted that the projection 19 is in the form of a set screw threaded into the body 18. As a result, a person can remove the set screw 19 and the cylinders 10 and 11 will completely separate. Because of this feature one can replace the springs 22 and 24 as desired.

Those skilled in the art will therefore understand that the appliance of the present invention is similar to that disclosed in U.S. Pat. No. 5,562,445 (hereinafter referred to as the '445 patent); but, the present invention utilizes two telescoping cylinders 10 and 11 in place of the cylinder and rod 12 and 14 of the '445 patent. As a result, the springs 22 and 24 can have almost twice the length of the spring 24 in the '445 patent. This extra length provides for much greater flexibility in forces exerted, over greater distances, without damaging, or overstressing, the springs.

FIG. 4 of the drawings illustrates a modified form of the device shown in FIGS. 1–3, and similar parts are designated by the primes of the numerals used in FIGS. 1–3. The basic structure will not be described again. The primary difference between the devices of FIG. 2 and FIG. 4 is that the device of FIG. 4 is not designed to be disassembled for replacement of springs. The device of FIG. 4 has the body 18' with guide pins 20' and 21', but the stop for the cylinders 10' and 11' is not carried by the body 18'. Rather, the stop for the cylinders 10' and 11' is created by flaring the cylinder 10' and swaging down the cylinder 11' as indicated at 28.

Those skilled in the art will readily devise several ways to assemble the device shown in FIG. 4; but, as here shown, the cylinders 10' and 11' are closed by end caps 29 and 30 respectively, the end caps 29 and 30 being welded, soldered or otherwise fixed to the cylinders. As a result, the cylinders can be flared and swaged to form the stop 28, then the cylinders can be assembled, the springs inserted, and the end caps installed.

The attachment means for the device of FIG. 4 includes a ball and socket arrangement as shown in the '445 patent for the cylinder 12', so no further discussion should be necessary. The attachment means for the cylinder 10' is also a ball and socket, but somewhat differently formed. It will be seen that a socket 31 is fixed to the cap 29, the socket 31 being crimpable so a ball 32 can be inserted, then the socket 31 crimped to hold the ball.

Figure 6:
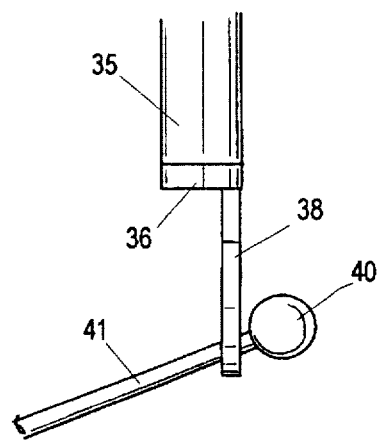
FIGS. 6 and 7 are front elevational views showing completion of the attachment means shown in FIG. 5; and, FIGS. 8 and 9 are cross-sectional views showing clamps for attaching an appliance of the present invention to an arch wire.
Figure 7:
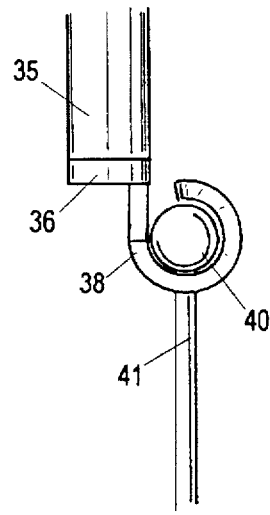

Another attachment means is illustrated in FIGS. 5, 6 and 7. One end of a cylinder 35 is shown, and those skilled in the art will understand that the cylinder 35 may be the inner cylinder, such as the cylinder 10 or 10', or may be the outer cylinder, such as the cylinder 12 or 12'. The cylinder 35 has an end cap 36 which carries an elongated tab 38, the tab 38 defining a slot 39 therein. The tab 38 is designed to be used with a ball; and, by way of example, FIGS. 6 and 7 show a ball 40 at the end of a pin 41.

FIG. 6 shows the pin 41 passing through the slot 39 in the tab 38. FIG. 7, then, shows the tab after it has been formed around the ball 40. Because of the elongated slot 39, the pin 41 can move rather freely while the ball 40 is held by the formed tab 38. It will be realized of course that the tab 38 can be formed in the opposite direction, so the ball is generally aligned with the cylinder 35, but as shown, the cylinder 35 will be farther away from the patient's teeth.

An orthodontic appliance such as that of the present invention is frequently installed by connecting it to an arch wire fixed to the patient's teeth. Thus, clamps, clips or the like are needed to effect the attachment easily. Otherwise, the orthodontist must tie the appliance to a bracket, or an arch wire, using pieces of wire. The clamps shown in FIGS. 8 and 9 are admirably adapted for use with the attachment means shown in FIGS. 4–7.

Figure 8:
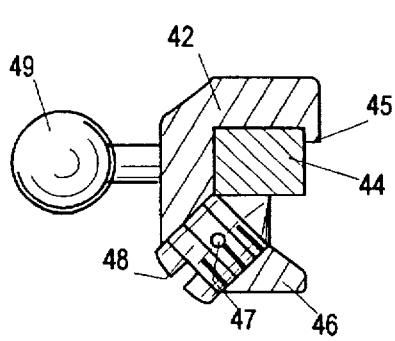

The clamp of FIG. 8 includes a base 42 covering two sides of the arch wire 44, and a finger 45 hooks behind the arch wire 44. The base 42 includes a member 46 having a set screw 48 located to engage the fourth side of the arch wire 44. Thus, with the set screw 48 removed, the base 42 can be manipulated to place the finger 45 behind the arch wire. The top and front of the arch wire are then covered by the base 42, and the member 46 is positioned beneath the arch wire 44. The set screw 48 can then be rotated until it abuts the arch wire 44 to hold the clamp in place, and a rod 47 of nylon or the like wedges within the threads to prevent inadvertent loosening of the set screw 48.

With the base 42 firmly held to the arch wire 44, there is a ball 49 extending from the base 42. Thus, the ball 49 may be the ball 32 for the ball and socket in FIG. 4, or may be the ball 40 in FIGS. 5–7.

Figure 9:
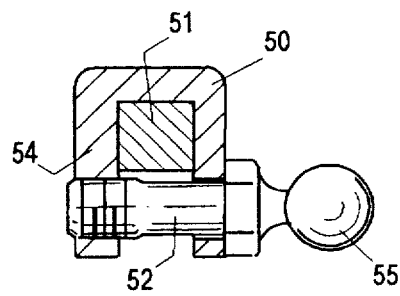

FIG. 9 shows a modification of the clamp of FIG. 8. The device in FIG. 9 comprises a U-shaped clevis 50 that engages three sides of the arch wire 51. A pin 52 extends through appropriate openings in the front and rear sides of the clevis 50. As here shown, the opening in the rear side 54 is threaded to mate with threads on the pin 52. The opening in the front side will be large enough for the threaded end to pass easily therethrough.

A ball 55 is carried at the end of the pin 52, and this ball can be used as discussed above with regard to FIGS. 4–7.

It will therefore be seen that the present invention provides an orthodontic appliance that is relatively easy to install, and that will provide the desired forces while allowing full normal movement of the mandible. All springs are fully enclosed so there is no danger of pinching tissue, and no places for food to collect. The attachment means are simple and versatile for use with any other appliances the patient may have.

It will of course be understood by those skilled in the art that the particular embodiments of the invention here presented are by way of illustration only, and are meant to be in no way restrictive; therefore, numerous changes and modifications may be made, and the full use of equivalents resorted to, without departing from the spirit or scope of the invention as outlined in the appended claims.

We claim:

1. An orthodontic appliance comprising a first substantially rigid cylinder having a first end and a second end, a second substantially rigid cylinder having a first end and a second end, said first cylinder being slidably received within said second cylinder, said second end of said first cylinder being open and said first end of said second cylinder being open, and a spring means within said cylinders extending from said first cylinder to said second cylinder, said first end of said first cylinder being closed for receiving one end of said spring means, and said second end of said second cylinder being closed for receiving the opposite end of said spring means, stop means for limiting sliding motion between said first and said second cylinders; and attachment means for fixing said appliance to a patient's teeth.

2. A orthodontic appliance as claimed in claim 1, wherein said spring means comprises a first spring within said first cylinder and a second spring within said second cylinder, a body between said first spring and said second spring, a first guide pin extending from said body and through said first spring, and a second guide pin extending from said body and through said second spring.

3. An orthodontic appliance as claimed in claim 2, wherein said first cylinder defines a slot therein parallel to the centerline of said first cylinder, said second cylinder defines a slot therein parallel to the centerline of said second cylinder, said stop means comprising a screw fixed to said body and extending through both said slot in said first cylinder and said slot in said second cylinder.

4. An orthodontic appliance as claimed in claim 2, wherein said second end of said first cylinder is flared outwardly and said first end of said second cylinder is swaged inwardly, said flared second end and said swaged first end constituting said stop means.

5. An orthodontic appliance as claimed in claim 1, and further including a third cylinder, said second cylinder being slidably receivable within said third cylinder, said third cylinder having a first end that is open for receiving said second cylinder and a second end that is substantially closed, said second end carrying a first part of said attachment means, said first end of said first cylinder carrying a second part of said attachment means.

6. An orthodontic appliance as claimed in claim 1, said attachment means comprising a socket and a ball received within said socket, said socket being crimpable for securing said ball therein.

7. An orthodontic appliance as claimed in claim 1, said attachment means comprising a tab extending from said first end of said first cylinder, and a ball, said tab being formable about said ball for securing said ball to said first cylinder.

8. An orthodontic appliance as claimed in claim 7, wherein said ball is fixed to a connector for connecting to an arch wire.

9. An orthodontic appliance as claimed in claim 8, wherein said connector comprises a base carrying said ball, and a set screw for securing said base to the arch wire.

10. An orthodontic appliance as claimed in claim 8, wherein said connector comprises a clevis for receiving an arch wire therein, and a pin receivable through said clevis for holding said clevis to said arch wire, said ball being fixed to said pin.

* * * * *